United States Patent [19]
Ross

[11] Patent Number: 5,094,099
[45] Date of Patent: Mar. 10, 1992

[54] CHROMATOGRAPHIC COLLECTION APPARATUS AND METHOD FOR SEQUENTIAL CONDENSED AND VAPOR PHASE SPECTROSCOPIC STUDIES

[76] Inventor: Ronald D. Ross, 308 N. Fourth Ave., Highland Park, N.J. 08904

[21] Appl. No.: 516,206

[22] Filed: Apr. 30, 1990

Related U.S. Application Data

[63] Continuation-in-part of Ser. No. 210,314, Jun. 23, 1988, abandoned.

[51] Int. Cl.⁵ ............................................. G01N 30/72
[52] U.S. Cl. .................... 73/23.37; 73/23.42; 73/864.81
[58] Field of Search .............. 73/23.42, 23.41, 23.4, 73/23.37, 864.81; 250/288; 422/89

[56] References Cited

U.S. PATENT DOCUMENTS
4,641,541  2/1987  Sharp .............................. 73/864.81

FOREIGN PATENT DOCUMENTS
2077775  11/1971  France .............................. 73/23.37

*Primary Examiner*—Hezron E. Williams
*Assistant Examiner*—Joseph W. Roskos
*Attorney, Agent, or Firm*—King & Schickli

[57] ABSTRACT

An apparatus and method are provided for conducting sequential condensed and vapor phase spectroscopic studies. The apparatus includes a vacuum manifold including a series of interconnected conduits forming a sealed chamber for containing a sample undergoing analysis. The vacuum manifold includes a collection/deposition station and a spectroscopy/revaporization station connected together by a transfer conduit. Ports in the vacuum manifold at the collection/deposition station connect the chamber to a vacuum pumping system and a chromatograph separates a sample to be tested into individual chemical compounds. A collection tube with a mechanism providing transport between stations is contained within the vacuum manifold. At the collection/deposition station, a separated compound from the chromatograph is deposited on a deposition surface of a collection tube. The tube is then shuttled for spectro analysis at the spectroscopy/revaporization station where ports allow the deposited sample to be subjected to a beam of electromagnetic radiation from an appropriate source. Detectors positioned at the ports both in and out of the plane of the incident beam allow analysis. After condensed phase study, a revaporization/collection mechanism allows the sample to be revaporized from the deposition surface of the collection tube and recovered for further vapor phase analysis.

16 Claims, 6 Drawing Sheets

CHROMATOGRAPHIC COLLECTION APPARATUS AND METHOD FOR SEQUENTIAL CONDENSED AND VAPOR PHASE SPECTROSCOPIC STUDIES

This application is a Continuation-in-Part of U.S. Pat. Application Ser. No. 210,314, filed June 23, 1988 and entitled "A Chromatographic Collection System for Sequential Condensed and Vapor Phase Spectroscopic Studies" now abandoned.

TECHNICAL FIELD

This invention relates to the field of analytic chemistry and, more particularly to the chromatographic analysis of chemical compounds. More specifically, the present invention relates to an apparatus and method for interfacing a chromatograph with various other instruments and equipment for analyzing compounds isolated by the chromatograph.

BACKGROUND OF THE INVENTION

In a chromatograph, an inert carrier substance (gas, liquid or supercritical fluid) is passed continuously at a controlled rate and temperature through a column consisting of a permeable stationary material contained in a tube. A sample containing compounds to be analyzed is injected into the carrier flow where it enters the column. Due to interaction with the stationary material of the column, various components of the sample travel along the column at different rates, and emerge at different times. Emerging compounds can be detected by any of a variety of methods, such as mass spectroscopy or flame ionization. Detector response can be continuously recorded, so that each emerging component shows up as a peak on the recording. The relative time of emergence of components of a mixture provides information as to the chemical nature of the compounds they represent, while the size of the peaks suggests the concentrations of the compounds.

Thus, it should be appreciated that chromatography may be utilized to (1) separate various compounds in the sample from each other, thereby allowing individual analysis by other methods, and (2) provide some qualitative and quantitative information about each of the compounds thus isolated.

While chromatographic information alone is not likely to be conclusive in identifying separated compounds, except in simple cases, the power of modern chromatographic analysis lies in combining chromatography results with additional sophisticated chemical and/or spectroscopic studies of the chromatographic effluent. In this way, many compounds may be readily and conclusively identified even when present in relatively small concentrations.

To date, chromatographic analysis has proven of particular value in such applications as quantitative analysis of organic pollutants. Still, improvements in both the equipment and techniques involved are desired. More specifically, the compounds of interest in pollutants are typically present in exceedingly low concentrations. Further, in many cases, only a limited amount of the material containing these compounds is available for analysis. In such applications, the amount of compound available can easily be the limiting factor in the accuracy of analysis.

Unstable compounds also present a significant problem as chemical alteration of the compound itself during preparation for analysis can be a source of error. The ideal method to overcome this difficulty would be to perform all the desired analyses in close sequence on a single unique sample of chromatographic effluent. This approach is, however, not possible because (1) some methods of analysis alter or destroy the compounds of interest, or because (2) present chemical devices do not provide for sequential performance of some analyses.

Accordingly, it should be appreciated that in these cases there is presently no ideal solution; that is to say:

Dividing the effluent from a single chromatographic injection into several smaller aliquots for several different analyses may significantly reduce the resolution of these analyses.

Avoiding this problem by using a separate chromatographic injection for each desired analysis is only feasible if the sample material is available in sufficient quantity, and introduces the possibility that the substances analyzed may not be identical.

In either case, there is the possibility that the material presented to one analysis may have undergone chemical alteration so it is no longer identical to the corresponding material subjected to another analysis.

In addition, any loss or inefficiency in collection, concentration, and presentation of these tiny samples for analysis is likely to reduce the resolution of the analysis.

Due to these considerations, any innovation is a significant advancement of art in this field if it: (1) makes it possible to perform previously incompatible analyses on a single effluent aliquot; (2) reduces the likelihood of alteration of compounds of interest in the interface; and/or (3) improves the efficiency of collection, concentration and presentation for analysis. In contrast to conventional approaches described below, the present invention achieves all three of these objectives.

At present, products of chromatographic separation are typically analyzed (1) by continuous monitoring of the effluent stream, or (2) by capturing selected time segments of the effluent stream for later study. For survey of mixtures of unknown composition, continuous monitoring is preferable, whereas for detailed study of selected sample components, capture offers significant advantages.

In continuous monitoring, the chromatographic effluent passes more or less directly into equipment designed for analysis "on the fly". The limitations of this approach in studies, for example, involving the absorbance of electromagnetic radiation (EMR) are reviewed by Griffiths et al (1983) with reference to FT-IR studies. Other "on the fly" methods involve an intermediate continuous sample-processing step, such as vaporization of the effluent from a liquid chromatograph before it enters a spectrometer. Because of the limited time available for observation of a given effluent component, these methods are limited by the speed of data acquisition of the detection system. Consequently, stop-flow techniques have been developed and used with continuous-monitoring systems to increase observation time for selected segments of the effluent stream. These, however, are typically awkward and meet with limited success.

The alternative to continuous monitoring—capture or immobilization of segments of the effluent stream—has the great advantage of allowing lengthy or repeated examination of the capture sample, to achieve a higher signal-to-noise ratio. Capture may be accomplished by (1) trapping in organic solution such as with an impinger, or (2) absorption on organic polymers with large surfaces such as TENEX{®}. Unfortunately, in ordinary laboratory methods the sample so captured must be transferred to a spectrometer (or other detection system), and one or more additional steps of preparatory processing may be required, each of which takes time and is a possible source of error.

A technique known as cryodeposition has been developed to address these problems. Performed under suitable conditions of temperature and pressure, cryodeposition can tend to isolate the sample compounds from the chromatographic carrier substance, eliminating the need for a separate sample-concentration step. Cryodeposition at extremely low temperatures has the additional advantage that certain compounds which could not be studied in conventional matrices because of decomposition will remain stable for long enough to allow testing.

In the devices described by Conrad et al., in U.S. Pat. No. 4,158,772, and manufactured under the trade name Cryolect by Mattson Instruments, the cryodeposition process occurs on a continuous cryogenic surface in an open vacuum chamber. In these devices, the chromatographic effluent is mixed with an inert and neutral matrix material such as argon gas, and the mixture is directed against a rotatable cooled sample block inside a vacuum chamber, so that a frozen spot or band of the matrix material containing some of the compounds separated by the chromatograph is deposited on the surface of the block. The vacuum chamber is provided with windows to permit spectroscopic examination of the immobilized samples in situ.

Still, despite these advantages, cryodeposition devices have a number of shortcomings:

(1) Because they are only capable of accepting gaseous-phase input, they cannot be used with liquid or supercritical fluid chromatographs without addition of intermediate effluent-processing equipment;

(2) There is little provision made for adjustment of the effluent jet, including its distance or attitude relative to the deposition surface, or of the temperature of the effluent, and no provision for any such adjustments in the course of a chromatographic run. This makes it impossible either to maximize the efficiency of capture of each compound, or to optimize the configuration of the frozen sample deposit for a particular spectrometer, as is crucial with small samples containing very dilute analytes.

With very small samples, maximum signal-to-noise ratio requires sample deposits configured for maximum interaction with the beam of electromagnetic radiation (EMR) from the particular spectrometer that will be used to study them. Roughly speaking, maximum interaction will be achieved when the beam of EMR from the spectrometer is directed at a sample deposit neither larger nor smaller than the beam diameter;

(3) Because deposition is on a locally unconfined surface, such adjustments would in any case have limited effect on the pressure gradient of the jet close to the collection surface, a factor which should be subject to control if optimum collection efficiency and deposit configuration are to be achieved;

(4) Though separate segments of the effluent stream are isolated by deposition at discrete locations on the sample block, there is no provision for recovering them from the device as discrete samples for further analysis by vapor phase methods; and (5) Because these systems require a large cryostat surface relative to the total deposition surface in an open vacuum chamber the vacuum chamber cannot be conveniently reduced to a small size or configured to facilitate recycling and cleaning.

SUMMARY OF THE INVENTION

Accordingly, it is a primary object of the present invention to provide an apparatus and method for efficiently and effectively interfacing a chromatograph with various other instruments and equipment adapted for analyzing chemical compounds as isolated by the chromatograph.

Another object of the present invention is to provide an apparatus and method that make it possible to study portions of effluent from gas, liquid or supercritical fluid chromatographs.

Still another object of the invention is to provide an apparatus including a deposition device permitting several adjustments to produce sample deposits of optimum dimensions and configuration for maximum interaction with the beam of the particular spectrometer that will be used to study them, in order to achieve the highest possible signal-to-noise ratio. Roughly speaking, maximum interaction will be achieved when the EMR beam from the spectrometer is neither larger nor smaller in diameter than the deposited sample.

An additional object of the invention is to provide a device and method allowing these and other adjustments of the cryodeposition device to be made as needed during the course of a single chromatographic run, so that as each compound of interest emerges from the chromatograph, the cryodeposition device can be adjusted for that particular compound, to achieve either (a) maximum efficiency or (b) maximum specificity in capture of that compound.

A further object of the present invention is to provide a method and apparatus making possible the study of portions of chromatographic effluent in the vapor phase subsequent to their condensed phase spectroscopic evaluation. This is achieved by performing cryodeposition in such a way that, after study of the samples in the solid phase is complete, each sample can be individually vaporized and transported by an inert carrier gas for further study in the vapor phase.

Yet another object of the invention is to facilitate recycling and cleaning of the collection device to maintain operating efficiency and to allow for rapid speed and determination.

Additional objects, advantages and other novel features of the present invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects and in accordance with the purposes of the present invention as described herein; an improved apparatus and method are provided for analyzing samples of chemical compounds. Advantageously, the apparatus and method allow for adjustable cryodeposition and subsequent recovery of discrete segments of a chromatographic effluent stream, with provision for spectroscopic examination of the deposited material prior to recovery for vapor phase study. Accordingly, the method and apparatus of this invention offer unique and useful advantages over other solutions to the above mentioned problems of interfacing chromatographic separation with the detection of compounds in the chromatographic effluent.

The apparatus of the present invention includes a vacuum manifold that forms a sealed chamber for holding a sample undergoing analysis. A gas chromatograph is connected to the vacuum manifold. The gas chromatograph serves to separate the various chemical compounds in the sample and carry them in an effluent stream into the sealed chamber of the manifold.

A collection tube is provided in the sealed chamber. The effluent stream from the chromatograph is directed so as to impinge upon a deposition surface on the collection tube where the separated chemical compound to be analyzed is deposited. A pump is connected to the manifold and in fluid communication with the sealed chamber so as to maintain a vacuum in the chamber during sample handling and analysis.

First, second and third optical windows are also provided in the manifold. A spectrometer electromagnetic radiation source is provided to direct electromagnetic radiation through the first optical window onto the compound deposited on the collection tube. An electromagnetic radiation detector is provided at the second and/or third optical windows to detect the electromagnetic radiation from the source either in and/or out of the plane of the source and thereby complete spectroscopic analysis.

Additionally, a revaporization and transfer mechanism is provided in the manifold. This mechanism may be selectively activated to revaporize the deposited compound and then transfer the compound to another instrument for additional vapor phase study.

More specifically, the apparatus includes a mechanism for conveniently shuttling the collection tube between a first, collection/deposition station where the compound is deposited on the collection tube and a second, spectroscopy/revaporization station where spectroanalysis and revaporization are completed. The shuttling mechanism is a relatively compact structure that is simple to operate while providing accurate movement of the collection tube. The mechanism includes (1) a support block for retaining the collection tube; (2) a cryogenic unit mounted to the support block for cooling the collection tube to a desired deposition temperature; (3) a mechanical support/cryogenic service conduit connected to and supporting the cryogenic unit within the sealed chamber and (4) a bellows for displaceably mounting the mechanical support/cryogenic service conduit to the manifold.

Preferably, the distal end of the bellows is mounted on a linear motion stage that is driven by a stepping motor. Such a system allows accurate, precise movement of the collection tube and, hence, control of the deposition geometry between the collection tube and the affluent stream from the gas chromatograph. An observation window provided in the manifold at the deposition station allows the operator to visually observe the deposition of the compound on the collection tube.

Still more specifically, the revaporization and transfer mechanism discussed above includes a displaceable revaporization manifold and means for moving this manifold between a first position away from the collection tube to a second position covering both ends of the collection tube. The revaporization manifold includes a revaporization block for receipt about the ends of the collection tube and a support/service conduit connected to the revaporization block. A purge gas delivery line runs along the conduit. The proximal end of the delivery line is connected to a pressurized source of purge gas. A distal end of the delivery line is connected to the revaporization block so as to be in fluid communication with one end of the collection tube when the block is in the second position. A purge gas and revaporized compound recovery line also runs along the conduit. The proximal end of the line is connected to the revaporization block so as to be in fluid communication with the opposite end of the collection tube when the block is in the second position. The distal end of the recovery line is connected to an additional vapor phase recovery apparatus, such as a chromatograph, mass spectrometer, etc.

The distal end of the support/service conduit of the revaporization and transfer mechanism is supported in a bellows mechanism that allows the displacement of the revaporization block between the first and second positions. One end of the bellows is mounted to the vacuum manifold. The other end of the bellows is mounted to a linear motion stage. This linear motion stage is connected to a stepping motor so as to allow precise movement of the revaporization block as desired to effect smooth and efficient operation of the apparatus.

In accordance with another aspect of the present invention, an improved vacuum manifold, as referred to above, is provided for interfacing various instruments and equipment utilized in analyzing samples of chemical compounds. The vacuum manifold comprises a series of interconnected conduits forming a sealed chamber. A first or deposition station formed by the interconnected conduits includes a first port for sealed connection and fluid communication with a chromatographic column. A second port provides sealed connection and fluid communication with a vacuum pumping system.

A second or spectroscopy/revaporization station formed by the interconnected conduits includes third, fourth and fifth ports sealed with optically pure windows. The third and fourth ports are substantially aligned with the fifth port in a plane substantially perpendicular to the third and fourth ports. Together, the third, fourth and fifth ports allow spectroscopic analysis of a sample.

The vacuum manifold also includes other unique features. More specifically, an observation port is provided at the first station to allow visual observation of the deposition process. Additionally, a transfer conduit connects the first and second stations. A sixth port at the first station aligned with the transfer conduit allows connection of the vacuum manifold to a means for displacing collection tubes within the manifold as described above in greater detail. Further, a seventh port at the second station allows the vacuum manifold to be connected to a means for revaporizing and transferring the sample from the collection tube.

In accordance with yet another aspect of the present invention, a collection tube for the deposition of a chemical compound undergoing spectroscopic analysis is disclosed and claimed. The collection tube includes a tubular body member formed of optically pure material, such as quartz, having a deposition surface. Preferably, this surface is polished with an optically active coating that is reflective of wavelengths of electromagnetic radiation to be utilized in spectroscopic analysis. A delivery port is provided at one end of the tube to receive delivery of a sample to be analyzed. An exhaust port is provided at a second, opposite end of the tube for exhausting the sample after revaporization.

The tubular body member may be either circular or oblong in cross section. The collection tubes of circular cross section are specifically adapted for receipt of a single discrete sample deposit. In contrast, tubes of oblong cross section have their wide dimension parallel to the direction of movement of the tubes within the vacuum manifold as previously described. Accordingly, discontinuous movement of an oblong tube produces a number of discrete sample deposits on the deposition surface. Alternatively, continuous movement produces a strip deposit with a time-segment of the effluent stream mapped along the tube.

In accordance with yet another aspect of the present invention, an improved method is provided for analyzing a sample of chemical compounds utilizing a system of collection tubes in a vacuum chamber. In this method, the sample is first separated into individual chemical compounds utilizing a chromatograph. The chromatographic effluent including the individual chemical compound or compounds to be analyzed is then passed through a suitable orifice from the dense phase of the chromatographic column into a vacuum manifold which is maintained at subambient pressure as required. This pressure drop causes an acceleration of the fluid resulting in a vapor jet which impinges on the deposition surface of a collection tube. Together, the pressure gradient in the collection tube and the position of the chromatographic column connection orifice in the y and z axis relative to the deposition surface (the direction of movement of the collection tube being the x axis) determine the nature of the chemical species which are collected. Advantageously, the mobile phase and more volatile impurities are drawn off by the vacuum system.

The deposition geometry, collection tube vacuum, and temperature of the deposition surface can be varied between and during chromatographic runs. As described in greater detail below, they may even be optimized to obtain deposition of a high percentage of a particular analyte. Further, if somewhat reduced efficiency of collection can be tolerated, the collection specificity can even be optimized for a particular compound. This advantageously allows the present method and apparatus to have either a separation or concentration effect on the chromatographic effluent during the collection for spectroscopic study.

When another analyte of interest reaches the chromatographic column connection orifice a new individual collection tube is positioned for collection of that particular analyte. Alternatively, if collection is not desired, the effluent is drawn off through the by-pass vacuum system.

Once the chromatographic separation of interest has been completed, the step of transferring the collection tube to the spectroscopy/vaporization station is initiated. At the spectroscopy/vaporization station, the step of spectroscopically analyzing the chemical compound deposited on the individual collection tube may be performed. Subsequent to analysis, are the steps of revaporizing and collecting the deposited sample for further vapor phase study.

Spectroscopic study can be performed by, for example, ultra violet absorbance, infra red absorbance, or fluorescence methods. More than one of these techniques can be employed on a single sample by aligning the collection tube ports sequentially with separate optical ports aligned with the distinct spectroscopic instruments. When these studies are completed, the revaporization manifold is attached to the collection tube for revaporization of the deposited sample. Revaporization is implemented by increasing the temperature of the deposition surface. The temperature of the deposition surface is increased by conduction from the revaporization manifold which may be heated as needed.

If the revaporization manifold is connected to a detector operating at reduced pressure, such as an electron impact mass spectrometer, then the revaporization may be assisted in some cases by reduction in pressure in the collection tube following connection to the vapor phase detection device.

In the vapor phase, the collected sample can be evaluated by such techniques as vapor phase chemiluminescence or mass spectroscopy. The vapor phase method utilized could as well be gas chromatography with any desired detection system.

Still other objects of the present invention will become readily apparent to those skilled in the art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawing, incorporated in and forming a part of the specification, illustrates several aspects of the present invention and together with the description serves to explain the principles of the invention. In the drawing.

Reference will now be made in detail to the present preferred embodiment of the invention, an example of which is illustrated in the accompanying drawing.

DETAILED DESCRIPTION OF THE INVENTION

Figure 1:
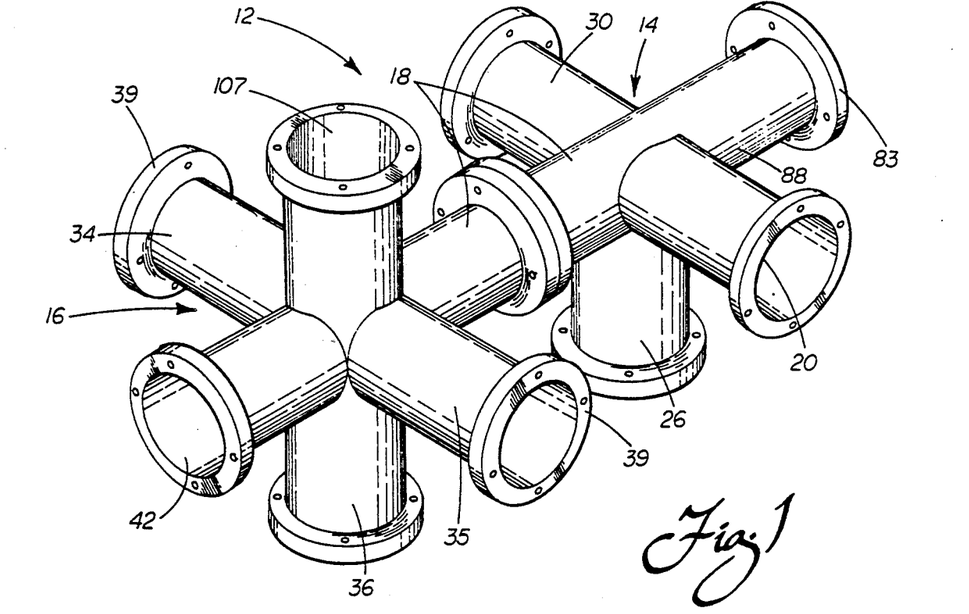
FIG. 1 is a perspective view of the vacuum manifold of the present invention.

Reference is now made to the drawing figures showing the improved apparatus 10 of the present invention for analyzing samples of chemical compounds. As best shown in FIG. 1, the apparatus 10 includes a vacuum manifold 12. The vacuum manifold 12 comprises a series of interconnected conduits that form a sealed chamber C for containing a sample undergoing analysis. The vacuum manifold 12 includes a collection/deposition station 14 and a spectroscopy/revaporization station 16 which are interconnected through a transfer conduit 18. More particularly the vacuum manifold 12 may be constructed by connection of a three-quarter inch five-way cross (VF-5075), for forming the collection/deposition station, with a three-quarter inch six-way cross (VF-6075), for forming the spectroscopy/revaporization station, as produced by Huntington Laboratories, Inc.

Figure 1A:
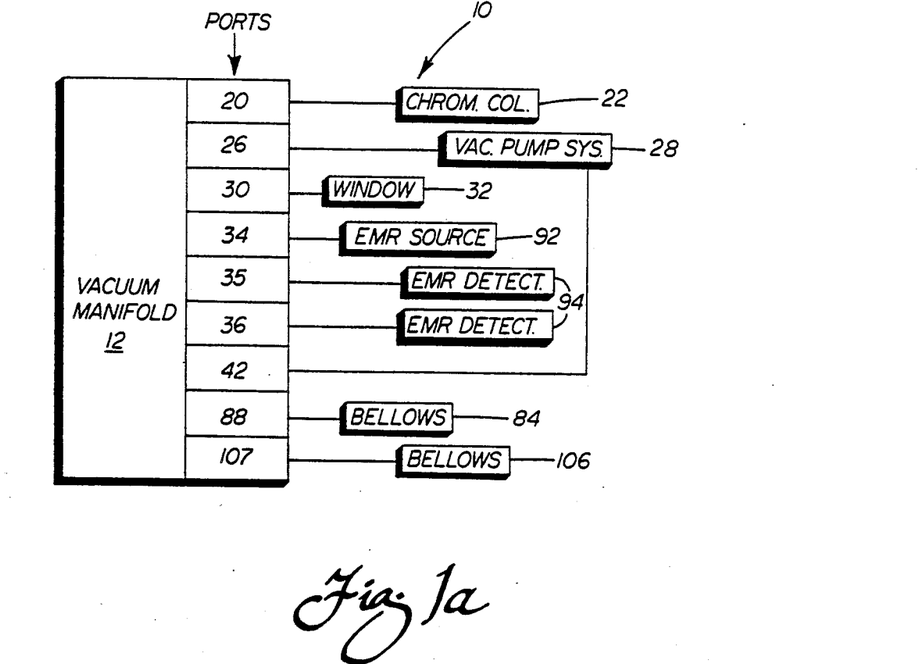
FIG. 1A is a schematic diagram showing the various connections of the components of the full apparatus of the present invention.
Figure 2:
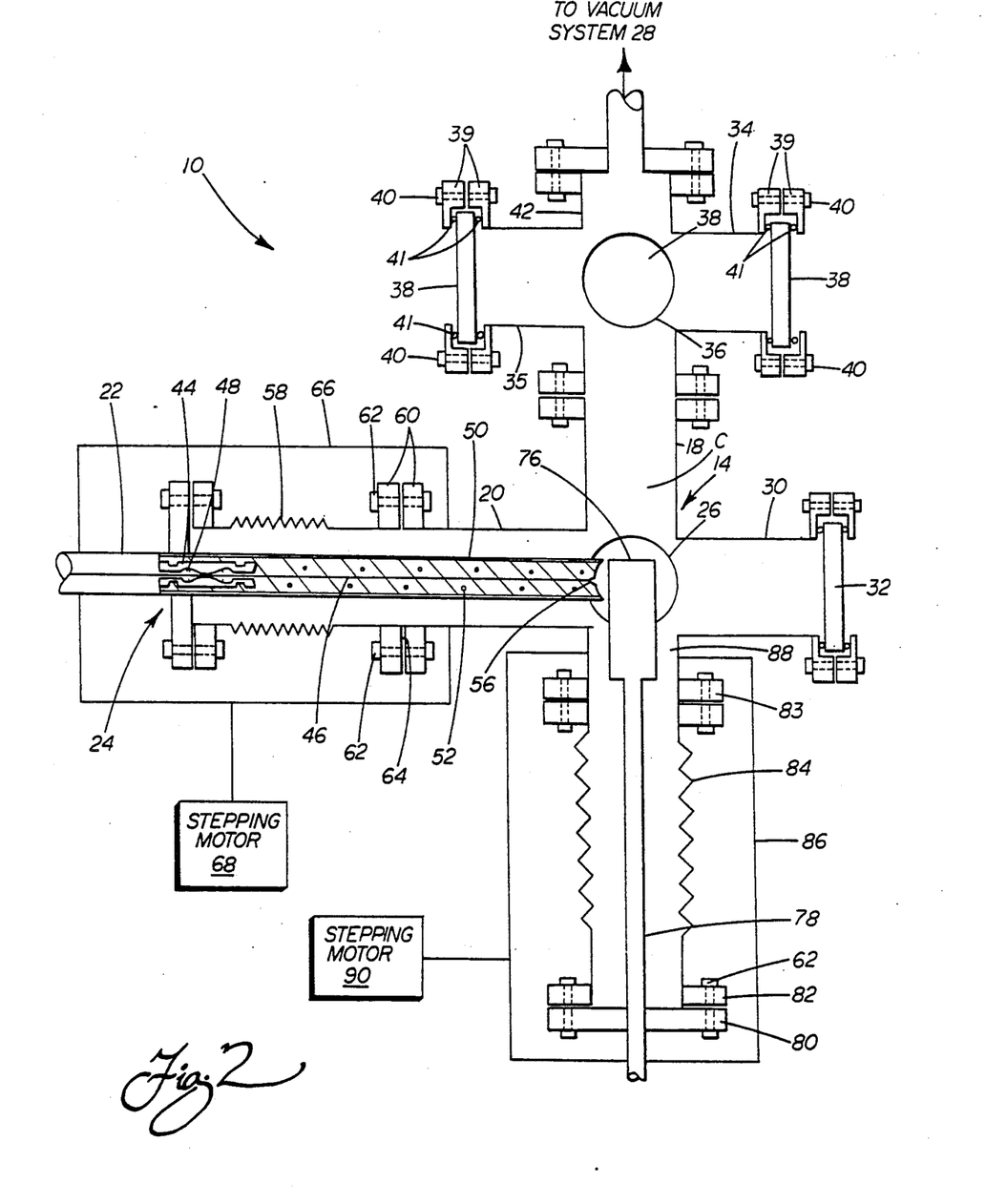
FIG. 2 is a sectional view schematically showing the collection tube support block positioned at the collection/deposition station.
Figure 3:
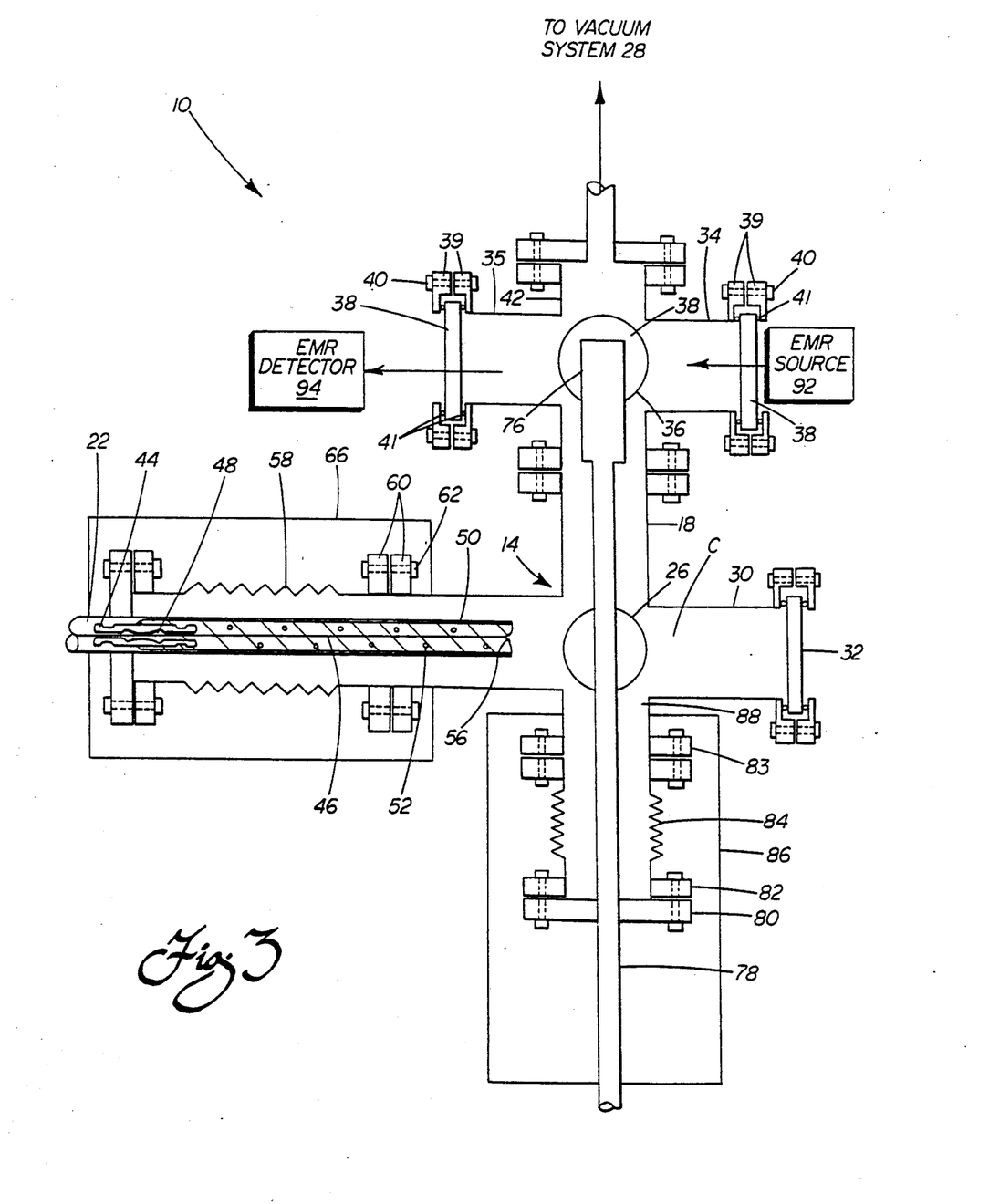
FIG. 3 is a view similar to FIG. 2 schematically showing the collection tube support block positioned at the spectroscopy/vaporization station.
Figure 4:
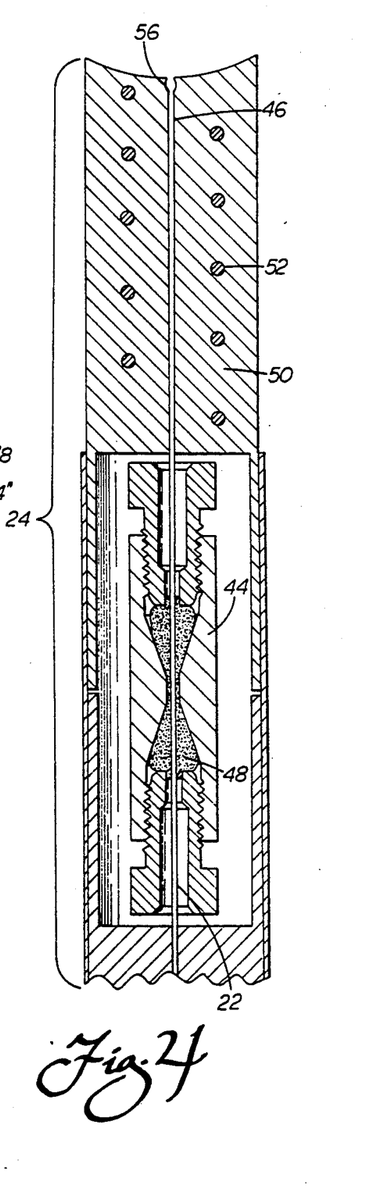
FIG. 4 is a cross-sectional view schematically showing the chromatographic column connection assembly.

As shown in FIGS. 1 and 1a, the collection/deposition station 14 includes a first port 20 for sealed connection to and fluid communication with a chromatographic column 22 through a connection assembly 24 (see also FIGS. 2-4). The collection/deposition station 14 also includes a second port 26 for sealed connection to and fluid communication with a vacuum pumping system 28 when operating in a bypass mode. Any type of vacuum pumping system may be utilized. For example, the pumping system 28, shown schematically in FIG. 1a, may include an oil diffusion pump such as the HS-2 diffusion pump manufactured by Varian Associates and a mechanical pump such as the 1402b-01 two-stage pump manufactured by Welsh. The mechanical pump is connected so as to be the only pump evacuating the vacuum manifold 12 or to alternatively act as a roughing/backing pump for the diffusion pump depending on the vacuum desired.

The collection/deposition station 14 also includes an observation port 30. The observation port 30 is sealed by a window 32 that allows visual observation of the deposition processes described in greater detail below.

The spectroscopy/revaporization station 16 includes three ports 34, 35, 36 that are each sealed with optically pure windows 38 (only one shown in FIG. 1) that allow spectroscopic analysis of the sample within the sealed chamber. More particularly, the windows 38 are each retained between cooperating flanges 39 held tightly together by fasteners, such as bolts, 40. An 0-ring 41 of vacuum stable material seals between the flanges 39 and the windows 38. The 0-ring 41 may be formed from Neoprene, Teflon or other appropriate inert material known in the art. An additional port 42 provided at the spectroscopy/evaporization station 16 is connected to and provides the main fluid communication with the vacuum pumping system 28 discussed above.

The method of analysis utilizing the present invention begins with the step of separating the sample to be analyzed into individual chemical compounds. This is done by utilizing the chromatographic column 22 which is connected to the collection/deposition station through the connection assembly 24. As best shown in FIG. 4, the chromatographic column 22 is connected by means of a restrictor coupler 44 to a flow restrictor 46. The restrictor coupler 44 accepts capillary gas chromatographic columns such as 0.30 mm OD fused silica capillary and has zero dead volume abutting the column 22 and the sealing vespule ferrule 48 directly against the flow restrictor 46. A commercial zero dead volume union such as is produced by VICI can be used.

A concentrically disposed restrictor support tube 50 envelopes the flow restrictor 46. More particularly, the support tube includes a heating element/sensor unit 52 connected to a proportional temperature controller 54 such as the CN310P2F manufactured by Omega Engineering. Together, the temperature controller 54 and heating element/sensor unit 52 serve to maintain the desired temperature of the flow restricter 46 and orifice 56 so as to provide the best separation and flow of sample in the effluent gas stream. As should be appreciated, the chromatographic column 22 may be connected to substantially any commercial capillary gas chromatographic such as is produced by Hewlett Packard.

As should also be appreciated from reviewing FIG. 2, the chromatographic column connection assembly 24 is mounted on a bellows 58 which is attached to the port 20 of the collection/deposition station 14. A vacuum connection is provided between the matching flanges 60 using fasteners 62. A copper gasket 64 seals between the flanges 60.

The bellows 58 is mounted on an X, Y positioner stage 66, shown schematically in FIG. 2, such as a CTC-515-2 manufactured by Control Techniques. Such a positioner stage 66 provides adequate precision of alignment. The positioner 66 is preferably controlled by a computer controlled stepping motor 68 allowing programmed alignment of the chromatographic column orifice 56 with a deposition surface 70 of a collection tube 72 (see also FIG. 5). Of course, manual control is also possible. In either event, during those periods in the chromatographic run when no collection is desired, the chromatographic column orifice 56 is placed in the bypass mode to direct the effluent jet below the collection tube 72 so that the effluent will pass into the vacuum pumping system 28 through the port 26.

Figure 5:
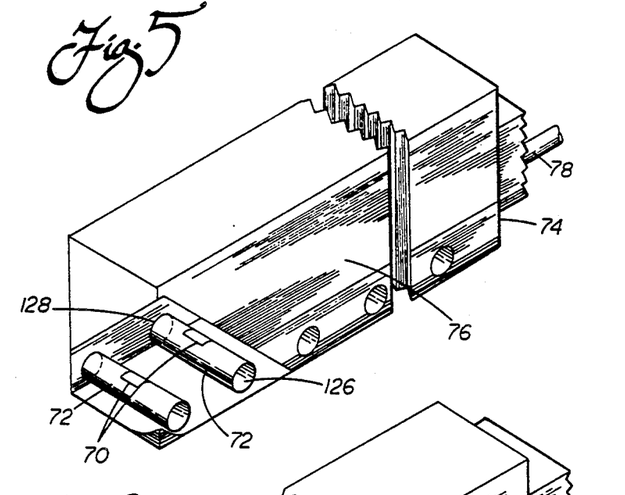
FIG. 5 is a partially cut-away perspective view schematically showing the collection tube assembly.

As best shown in FIG. 5, one or more collection tubes 72 are held in a collection tube support block 74. A cryogenic unit 76 is mounted to the support block 74. The cryogenic unit 76 serves to cool the collection tube 72 through the support block 74 to a desired deposition temperature for the collection of a sample for analysis. As best shown in FIGS. 2-3 and 5, a mechanical support/cryogenic service conduit 78 is connected to and supports the cryogenic unit 76. A Joule-Thompson device such as is manufactured by MMI, Inc. provides adequate cryogenic service through the conduit 78.

Movement of the collection tube 72 within the sealed chamber between the collection/deposition station 14 and the spectroscopy/revaporization station 16 is achieved by mounting the support/service conduit 78 on a flange 80 which is attached to a flange 82 of bellows 84. The bellows 84 is mounted on a linear motion stage 86. To construct this assembly, a bellows 84, such as the 247-11 bellows manufactured by Huntington Laboratories is welded to vacuum flanges such as the 275-133-062 manufactured by Huntington Laboratories. The constructed assembly may then be attached to the vacuum manifold flange 83 at port 88 of the collection/deposition station 14. A stepping motor 90 drives the linear motion stage so that the alignment of the deposition surface 70 with the effluent jet from the orifice 56 is controlled at any particular time in the course of the chromatographic run manually or, more preferably, by a computer program. The linear motion stage 86 may, for example, be an ATS-100-150 manufactured by Aerotech Stage.

Advantageously, depending on the operating parameters, compounds within a specific range will be deposited. Thus, it should be appreciated that by adjusting (1) the temperature of the effluent gas stream, (2) the temperature of the deposition surface 70 utilizing the cryogenic unit 76, (3) the relative orientation geometry of the orifice 56 to the deposition surface through adjustment of the positioner stage 66 and linear motion stage 86, and (4) the vacuum pressure at the collection tube 72 exhaust port 128, operation parameters may be optimized to obtain deposition of a high percentage of a particular analyte. Stated another way, fine tuning of the device is provided to allow for maximum efficiency in the collection of a sample with optimization for a particular compound possible.

For example, with the deposition surface at 150° Kelvin and the pressure in the vacuum manifold 12 at 0.05 torr efficient collection of benz[a]anthracene is accomplished.

Following the depositing of an individual chemical compound sample on a deposition surface of a collection tube 72, the stepping motor 90 is activated to shuttle the support block 74 and collection tube 72 contained therein through the transfer conduit 18 to the spectroscopy/revaporization station 16. There a spectroscopic analysis of the deposited chemical compound may be completed.

More particularly, the collection tube 72 including the deposited sample to be analyzed is positioned in alignment with the optical windows 38, of the ports 34, 35. A spectrometer electromagnetic radiation source 92 is aligned with the optical window at port 34 so as to direct radiation through the window onto the sample on the deposition surface 70. For ultraviolet absorbance, the beam of ultraviolet light traveling from the spectrometer source 92 is directed to impinge upon the sample. One or more detectors 94 are then positioned in plane at the window to port 35 to detect radiation passing through the sample. Of course, infrared and visible light studies may also be completed.

Figure 8:
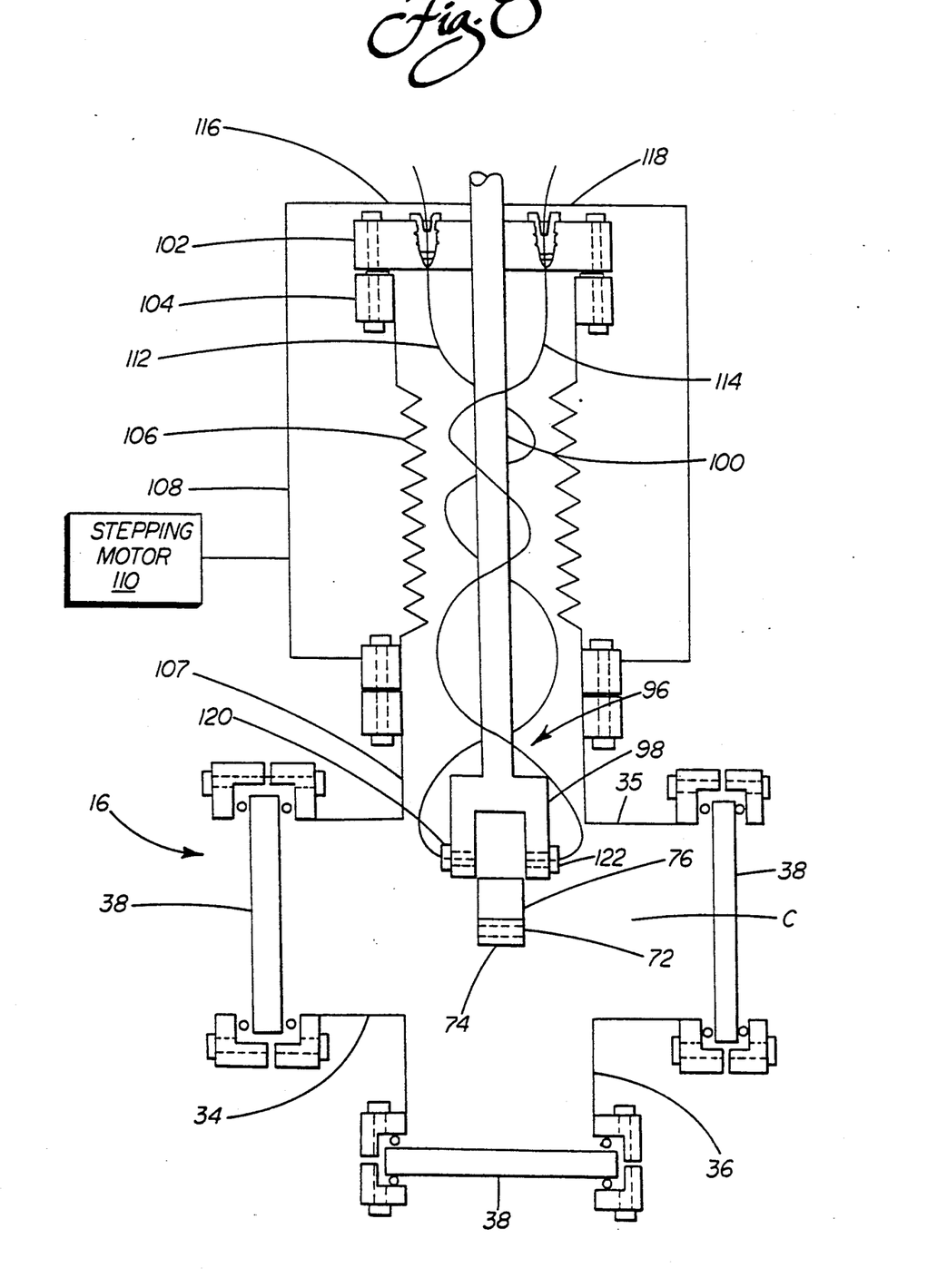
FIG. 8 is a sectional view schematically showing the spectroscopy/revaporization station with the collection tube support block in position for spectroscopic studies.
Figure 9:
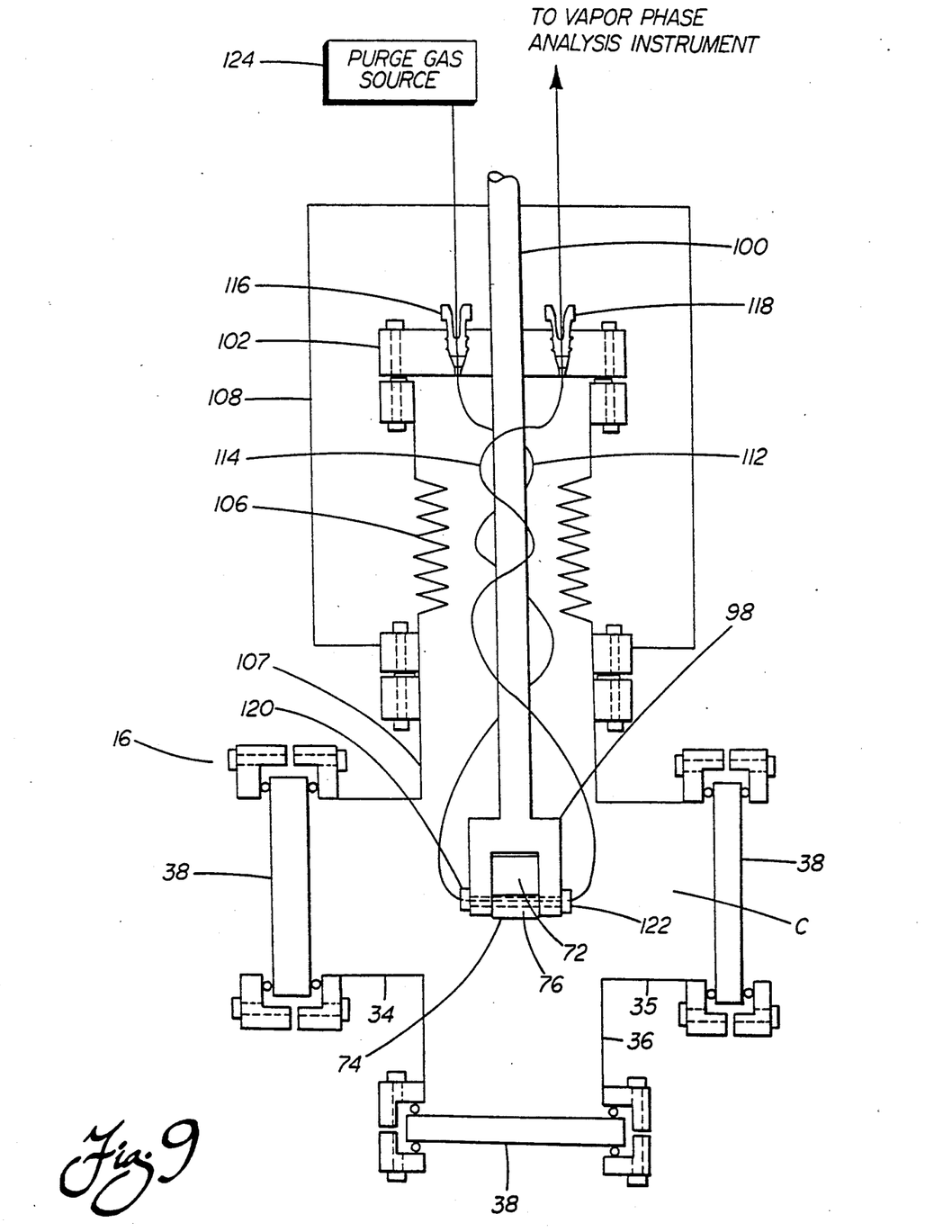
FIG. 9 is a sectional view schematically showing the spectroscopy/revaporization station with the revaporization manifold and collection tube support block in position for revaporization.

Following complete spectro analysis, is the step of revaporizing the chemical compound sample from the deposition surface 70. More particularly, as best shown in FIGS. 8 and 9, the apparatus 10 includes a displaceable revaporization manifold 96. The revaporization manifold 96 may be moved from a first, rest position away from the support block 74 and collection tube 72 (note FIG. 8), and a second, operative position wherein the revaporization manifold covers both ends of the collection tube (note FIG. 9).

More specifically, the revaporization manifold 96 includes a substantially U-shaped revaporization block 98 for receipt about the ends of the collection tube 72. A support/service conduit 100 is connected to the revaporization block 98. The conduit 100 provides service such as electric power to a combined heating and sensing unit (not shown) in the revaporization block 98.

As shown in FIG. 8 and 9, the support/service conduit 100 is mounted to a flange 102 fastened to a cooperating flange 104 of a bellows 106 which is mounted to port 107 of the vacuum manifold 12 in same manner as bellows 58 and 84 previously described. The bellows is attached to a linear motion stage 108 such as the VF-075 model manufactured by Huntington Laboratories. This linear motion stage is driven by a stepping motor 110 in a manner known in the art to move or displace the revaporization block 98 between the rest and operative positions shown in these figures.

A purge gas delivery line 112 and a purge gas and revaporized sample recovery line 114 are sealed to the flange 102 by the pressure fittings 116, 118, respectively. The discharge or distal end of the delivery line 112 is sealed to the revaporization block 98 by the pressure fitting 120. Similarly, the proximal or entry end of the recovery line 114 is sealed to the revaporization block 98 by the pressure fitting 122.

In the revaporization position shown in FIG. 9, there is a continuous sealed path from a pressurized source of purge gas 124 through the delivery line 112 and over the deposition surface 70 in the collection tube 72 to the recovery line 114. Once the revaporization block 98 is in the revaporization position, cryogenic working fluid flow in the cryogenic unit 76 attached to the collection tube support block 74 is interrupted. The collection tube 72 is then allowed to thermally equilibrate with the revaporization block 98. After this equilibration, revaporization is performed by passing heated purge gas through the collection tube 72. For example if the purge gas is helium heated to 250° C., efficient transfer of deposited benzanthracene can be accomplished. As the sample is revaporized, it is drawn off through the recovery line 114 and may in fact be directed and delivered to additional analysis instruments for vaporization studies.

After all of the collected sample of interest has been transferred for vapor phase study, the revaporization block 98 is retracted to the first position and the system is purged.

More particularly, any residual sample material is removed from the revaporization block 98 by heating. The vacuum is also increased within the chamber through adjustment of the vacuum pumping system 28. This serves to draw off any residual materials which could be present through the port 42. Next the collection tube support block 74 is returned to the collection/deposition station 14 and the vacuum in the vacuum manifold is readjusted to the desired operating pressure. Finally, the deposition surface 70 of the collection tube 72 is cooled to the desired deposition temperature.

As should be appreciated from the preceding description, an important aspect of the present invention relates to the design of the collection tubes 72. As best shown in FIG. 5, each collection tube includes a tubular body member upon which is provided a deposition surface 70. Each collection tube 72 is also open at each end thereby including a delivery port 126 for the delivery of one or more chemical compounds as described above and an exhaust port 128 at the opposite end of the tube for exhausting the sample chemical compound upon revaporization. As should be appreciated, the tubular wall of the collection tube 72 is extended beyond the deposition surface 70. This serves to better maintain the pressure gradient for a more controlled and concentrated deposition of the sample.

In accordance with still another aspect of the present invention, the deposition surface is polished with an appropriate coating that is reflective of the wavelengths of electromagnetic radiation which are to be used in the spectroscopy studies.

Figure 7:
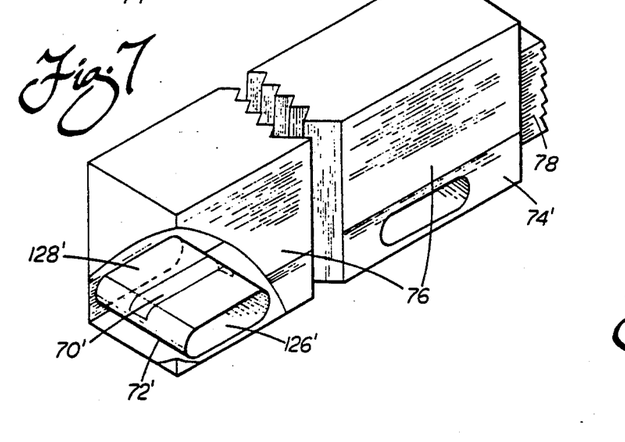
FIG. 7 is a view similar to FIGS. 5 and 6 schematically showing an alternative construction of the collection assembly incorporating elongated or oblong collection tubes.

It should also be appreciated that various modifications to the above described embodiment of the invention are possible. For example, collection tubes 72' having a single extended or oblong axis are shown in FIG.

7 supported in a collection tube support block 74' that is connected to a cryogenic unit 76 as described above. As shown, the collection tubes 72' are elongated along the axis of motion of the support blocks 74 between the first and second stations. More particularly, the collection tube 72' is constructed so that the length is a multiple of the optical focus diameter. Once again, the collection tube 72' includes entry and exit ports 126', 128' and a deposition surface 70'. Advantageously, the elongation of the tube 72' allows the study of the deposit formed by continuous deposition within a single tube during a chromatographic run or a portion of a chromatographic run. More specifically, if the stepping motor 90 is driven continuously during the deposition process, the position of the deposit on the deposition surface 70' will be a function of the chromatographic retention time. The relation between the chromatographic retention time and the deposition position can be changed during the course of the chromatographic run to optimize deposition for the types of condensed phase study that will be performed. Accordingly, such an elongated collection tube configuration and mode of operation allows condensed phase scanning of a single affluent peak at different positions to determine homogeneity or study of one or more resolved peaks.

Figure 6:
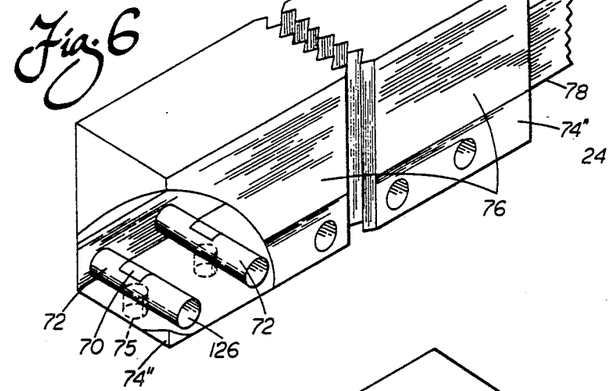
FIG. 6 is a view similar to FIG. 5 schematically showing an alternative construction of the collection tube assembly incorporating windows for studies of EMR out of the plane of source EMR beam.

In another alternative embodiment, the collection tube 72 shown in FIG. 6 is held in a collection tube block 74" including a port or an optical window 75. This window 75 is constructed of materials transparent to the wavelength of electromagnetic radiation of interest. As should be appreciated, the window 75 lies in a plane substantially parallel to the direction of travel of the electromagnetic radiation beam from the source 92. The window 75 is also aligned with the sample deposition surface 70 and the port 36 of the vacuum manifold thereby allowing for the study of radiation out of the plane of the source beam. This advantageously allows for the study of scattered or emitted light out of the plane of incident light. This modification facilitates the performance of fluorescense, Raman and Rayleigh spectroscopy. More specifically, the emitted or scattered light travels through the window 75 and window sealed port 36 to a detector 94.

It should also be appreciated that any collection tube 72 or 72' may be modified to provide for internal reflectance for making the surface of the collection tube opposite the deposition surface 70 reflective to the wavelengths of EMR of interest. This modification can provide increased sensitivity in absorbance studies by allowing multiple passes of EMR through the sample.

In summary, numerous benefits have been described which result from employing the concepts of the present invention. Advantageously, the apparatus of the present invention provides for the convenient handling of chemical compound samples undergoing analysis. It also allows for very effective and efficient handling and provides the ability to complete both spectroscopy and vapor phase studies on the same sample. This represents a significant advance in the art.

The foregoing description of the preferred embodiment of the invention has been presented for purposes of illustration and description. It is not intended to be exhaustive or to limit the invention to the precise form disclosed. Obvious modifications or variations are possible in light of the above teachings.

For example, the apparatus could include a modified chromatographic column connector that allows operation with a liquid chromatograph. More specifically, a liquid chromatographic column could be connected to a teflon transfer line and this transfer line to the restrictor coupler 44. The teflon transfer line would serve to thermally insulate the liquid chromatographic column from the chromatographic column connector assembly 24. Providing that minimal resistance to flow occurs in the restrictor, this form of the device will operate with a liquid chromatograph.

It should also be appreciated that the chromatographic column connection assembly 24 could be modified to allow for the operation of the invention with a supercritical fluid chromatograph. The resistance to flow of the restrictor would, however, need to be increased to the extent that the pressure of the mobile phase is above the critical pressure of the mobile phase at the operating temperature.

The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. An apparatus for analyzing samples of chemical compounds, comprising:
   manifold means forming a sealed chamber for holding a sample undergoing analysis;
   chromatograph means for separating different chemical compounds from said sample and carrying said compounds in an effluent stream, said chromatograph means being connected to said manifold means and in fluid communication with said sealed chamber;
   a collection tube received in said sealed chamber, said collection tube including a deposition surface upon which said compounds from said effluent stream are deposited;
   pumping means connected to said manifold means and in fluid communication with said sealed chamber so as to maintain a vacuum in said chamber;
   a first optical window provided in said manifold means;
   a spectrometer electromagnetic radiation source for directing electromagnetic radiation through said first optical window onto said compound deposited on said collection tube;
   a second optical window provided in said manifold means;
   means for detecting through said second optical window electromagnetic radiation from said spectrometer electromagnetic radiation source interacting with said deposited compound; and
   means received within said sealed chamber for revaporizing and transferring said deposited compound from said collection tube for additional vapor phase study.

2. The apparatus set forth in claim 1 further including means for shuttling said collection tube between a first station where said compound is deposited on said collection tube and a second station where spectro analysis of said deposited compound is completed.

3. The apparatus set forth in claim 2, wherein said shuttling means includes a collection tube support block for retaining said collection tube, a cryogenic unit mounted to said support block for cooling said collection tube to a desired deposition temperature, a mechanical support/cryogenic service conduit connected to and supporting said cryogenic unit; and bellows means for displaceably mounting said mechanical support/cryogenic service conduit to said manifold means.

4. The apparatus set forth in claim 3, wherein said bellows means is mounted on a linear motion stage that is driven by a stepping motor so as to allow adjustment of the deposition geometry between the collection tube and the effluent stream of the gas chromatograph means.

5. The apparatus set forth in claim 1, wherein said manifold means includes a collection/deposition station and a spectroscopy/revaporization station and an observation window is provided in said manifold means at said deposition station.

6. The apparatus set forth in claim 5, wherein a third optical window is provided in said manifold means; said second and third optical windows being provided at said spectroscopy/revaporization station, one of said second and third windows being provided in substantial alignment with said first window and said spectrometer electromagnetic radiation source and another of said second and third windows being provided in a plane substantially perpendicular to said first window.

7. The apparatus set forth in claim 1, wherein said revaporizing and transferring means includes a displaceable revaporization manifold and means for moving said revaporization manifold from a first position away from said collection tube to a second position covering both ends of said collection tube.

8. The apparatus set forth in claim 7, wherein said revaporization manifold includes a revaporization block for communication with the ends of said collection tube and a revaporization support/service conduit connected to said revaporization block.

9. The apparatus set forth in claim 8, further including a purge gas delivery line and a purge gas and revaporized compound recovery line, a proximal end of said delivery line being connected to a pressurized source of purge gas and a distal end of said delivery line being provided in communication with one end of said collection tube when said revaporization manifold is in said second position; a proximal end of said recovery line being in communication with the opposing end of said collection tube when said revaporization manifold is in said second position and a distal end of said recovery line being in communication with an additional vapor phase study apparatus.

10. The apparatus set forth in claim 8, further including second bellows means for displaceably mounting said revaporization support/service conduit to said manifold means.

11. The apparatus set forth in claim 10, wherein said second bellows means is mounted on a second linear motion stage that is driven by a second stepping motor so as to allow advancing and retracting of said revaporization manifold between the first and second positions.

12. A method of analyzing a sample of chemical compounds utilizing a system of collection tubes in a vacuum chamber comprising the steps of:
separating individual chemical compounds in said sample;
depositing an individual chemical compound on a deposition surface of a collection tube;
spectroscopically analyzing said deposited chemical compound;
revaporizing said chemical compound from said deposition surface;
collecting said revaporized chemical compound for further vapor phase analysis.

13. The method set forth in claim 12, including enclosing said chemical compound in a single vacuum chamber for said separating, depositing, spectroscopically analyzing, revaporizing and collecting steps.

14. The method set forth in claim 12, including transferring said collection tube from a first station where the depositing step is completed to a second station where the spectroscopically analyzing step is completed.

15. The method set forth in claim 12, wherein said vaporizing step includes the step of passing a heated effluent over said chemical compound on said deposition surface.

16. The method set forth in claim 12, including purging said vacuum chamber after said collecting step.

* * * * *